United States Patent [19]

van Rijckevorsel et al.

[11] Patent Number: 4,578,716
[45] Date of Patent: Mar. 25, 1986

[54] METHOD OF AND APPARATUS FOR MAKING A TEST STRIP AND A TEST STRIP MADE BY SUCH METHOD

[75] Inventors: Rainer van Rijckevorsel; Joachim Kasielke, both of Brühl; Heinz Macho, Mannheim; Peter Schäfer, Ludwigshafen; Klaus Nenninger, Mannheim, all of Fed. Rep. of Germany

[73] Assignee: Boehringer Mannheim GmbH, Mannheim, Fed. Rep. of Germany

[21] Appl. No.: 630,899

[22] Filed: Jul. 16, 1984

[30] Foreign Application Priority Data

Jul. 23, 1983 [DE] Fed. Rep. of Germany ....... 3326689

[51] Int. Cl.⁴ .............................................. G11B 5/00
[52] U.S. Cl. ....................................... 360/1; 360/137; 427/2
[58] Field of Search ........................... 360/1, 137, 101; 235/493; 346/33 ME; 428/611; 427/128, 131, 293, 2; 156/252, 253

[56] References Cited

U.S. PATENT DOCUMENTS

| | | | |
|---|---|---|---|
| 2,648,589 | 8/1953 | Hickman | 360/101 |
| 2,798,725 | 7/1957 | Marshall | 360/101 |
| 2,986,725 | 5/1961 | Dirks | 360/101 |
| 3,460,153 | 8/1969 | White | 346/33 |
| 3,715,570 | 2/1973 | Weichselbaum et al. | 360/1 |
| 4,164,320 | 8/1979 | Irazaquoi et al. | 235/493 |
| 4,420,353 | 12/1983 | Levine | 156/252 |
| 4,476,149 | 10/1984 | Poppe et al. | 427/2 |

FOREIGN PATENT DOCUMENTS

| | | | |
|---|---|---|---|
| 0073056 | 3/1983 | European Pat. Off. | |
| 2252857 | 5/1973 | Fed. Rep. of Germany | 360/1 |
| 913798 | 12/1962 | United Kingdom | 360/1 |

OTHER PUBLICATIONS

IBM-TDB, vol. 19, No. 9, Feb. '77, S. Kambic, Magnetic Encoder for Printer Terminal.
IBM-TDB, vol. 14, No. 3, Aug. '71, L. A. Joyce, Oscillating Transducer.
IBM-TDB, vol. 19, No. 5, H. Mueller, Magnetic Stripe Reader-Writer with Improved Head Suspension.
IBM-TDB, "Printed and Magnetic Encoded Merchandise Tag", Hagopian et al.; vol. 13, No. 9: Feb. '71.

Primary Examiner—Raymond F. Cardillo, Jr.
Assistant Examiner—Alyssa H. Bowler
Attorney, Agent, or Firm—Felfe & Lynch

[57] ABSTRACT

Method of and apparatus for making a test strip and a test strip made by such method having a longitudinally extending carrier and a test field thereon. The carrier has a layer of magnetizable material thereon in which an amount of data for the storage of information has been applied in the longitudinal direction of the magnetizable material. The carrier has a recess near each end thereof adapted to provide a required alignment and positioning of the strip.

32 Claims, 5 Drawing Figures

METHOD OF AND APPARATUS FOR MAKING A TEST STRIP AND A TEST STRIP MADE BY SUCH METHOD

The present invention is concerned with a method and apparatus for making a test strip, and to a test strip made by such method.

More particularly, the present invention is concerned with a process for the production of a test strip which usually has a longitudinally extending carrier made of a synthetic resin material and at least one test field. For the production thereof, a band of test field material is arranged on a broad band of the carrier material parallel to the longitudinal edges thereof, the band of the carrier material is provided with a quantity of data for the storage of information and the band as a whole is divided up, transversely to the direction of production, into a plurality of longitudinally extending test strips.

European patent specification No. 0,073,056 describes such a process and also the corresponding analysis strips. By means of such test strips, analytical determinations, especially for medical purposes, can be carried out with especially simple handling. Thus, for example, urine test strips are generally briefly dipped into a sample of urine and subsequently simply allowed to drip off. For blood investigations, a drop of blood is normally applied to the test field and after the test field is completely soaked, the residue is wiped off. A chemical reaction takes place in the test field between the reagents present therein and the components of the liquid applied. The colour change which takes place was previously evaluated visually but today appropriate apparatus are also available for a quantitative evaluation of the colour change. Thus, in particular, reflection photometers are used by means of which the degree of reflection of the test field after conclusion of the reaction can be determined at one or more wavelengths. The test fields usually consist of papers or fleeces which have been impregnated with appropriate reagents and dried or of reaction films, the test fields being either self-supporting or applied to carrier films. For the storage and read-off of the data of individual production batches, which is essential for the evaluation, in the case of the known test strips, a bar code is provided on the lower side thereof. This bar code contains batch-specific information and, in particular, an appropriate mathematical function for the calculation of the particular dependency of the concentration of the substance to be analysed to the particular degree of reflection. Information regarding the position of the function curve, batch-specific corrections and the like can be read off in an appropriate reflection measurement apparatus and can be processed in an appropriate manner, especially by means of a microprocessor.

Whereas coding with the help of a bar code is sufficient for some simple tests, the further development of test strips for the most varied blood and serum parameters requires the storage of an amount of data of the order of magnitude of at least 500 bit. However, in the case of test strips of this kind, which have a length of about 10 cm., with the help of a bar coding there can only be stored an amount of data of the order of magnitude of 50 bit. A larger amount of data would require either a correspondingly long test strip of the bars would have to be applied extremely finely, for which purpose, in practice, suitable printing or impressing systems are not available.

In the search for a possibility of applying a larger amount of data to test strips, the difficult limiting conditions have to be observed which result from the peculiarity of this product and of its production. On the one hand, because of its small size, very little space is available on the test strip for the application of data. On a typical test strip, the utilizable length for the application of information is limited to about 4 cm. For this reason, a high information density is necessary. On the other hand, the fact that these test strips are products which are produced in very large numbers, means that the production process must take place quickly and economically. Typically, about 400 test strips are produced per minute so that the coding must also be applied at an appropriate speed. The environmental conditions in the production of test strips are unfavourable for a sensitive process for the application of information.

Therefore, it is an object of the present invention to provide a process for the production of a test strip of the above-described type which permits a rational and economic application of an amount of data especially of the order of magnitude of at least 500 bit. The amount of data is to be arranged dependably on the test strip and error free reading in an evaluation device is to be ensured in the case of easy handling. Having regard to an economic production of the test strips in large numbers, the application of the amount of data is to take place in a short period of time.

Thus, according to the present invention, there is provided a process for the production of a test strip with a longitudinally extending carrier and a test field, in which a band of test field material is arranged on a broader band of carrier material substantially parallel to the longitudinal edges thereof, the band of the carrier material being provided with an amount of data for the storage of information, and in which the whole band is divided up transversely to the production direction into a plurality of longitudinally extending test strips, wherein the band of carrier material is provided in the region of at least one of its two longitudinal edges with a row of substantially equidistant recesses and on to the band of the carrier material there is applied, in the production direction, a layer of magnetizable material, the recordal of the amount of data in the layer of magnetizable material taking place transversely to the production direction.

The test strip produced by the process according to the present invention is characterized in that it has a layer of magnetizable material in which an amount of data is applied in its longitudinal direction and that each end of the carrier has a recess.

The recesses are preferably round holes. In the following specification, without limitation of the generality, for the purpose of simplicity, only the term "hole" is used instead of "recess". It will be understood, however, that the term "recess" as used in the claims, includes, without limitation, the term "hole".

The process according to the present invention makes possible, in the case of a high output, a dependable production of the test strips and also a reliable application of data and in particular of a large amount of data of the order of magnitude of at least 500 bit. By means of the rows of holes, there is achieved a good guiding of the band of the carrier material and also of the whole band during the production process. If both longitudinal edges of the band are provided with a series of holes, the holes preferably lying opposite one another, then, by means of two holes lying opposite one another transversely to the direction of production, there is provided a definite axis in the longitudinal direction of the test strip in question. This axis lies transversely to the direction of production and the application of the amount of data in the magnetizable layer takes place very exactly in the said direction. For reading off the amount of data by means of an evaluation apparatus, due to the said two holes, an exact geometrical axis is also provided. An angular displacement between the recording direction in the case of production and the reading-off direction is avoided in an especially simple manner. The rows of holes of the band of the carrier material and the hole present in each end of the finished test strip provide an exact positioning and alignment of the band or of the test strip. According to the present invention, the band is cut up transversely to the direction of production between the equidistant holes of both series of holes to give longitudinal test strips.

In an especially important embodiment of the present invention, before cutting up the whole band, the applied amount of data is read off for testing purposes. If an error is ascertained, an appropriate marking is provided in order, after cutting up, to be able to sort out the faulty test strips. Such a marking is provided especially in the form of a coloured spot in order to make possible a simple and dependable sorting out. However, some other kind of marking can be used, for example also a non-visible one, such as a magnetic marking.

In a special embodiment of the present invention, the layer of magnetizable material is applied in the form of a previously produced magnetic band, for example by adhesion, fusion adhesion or the like. Within the scope of the present invention, this can take place before, during or also after the application of the band of test field material. The bonding of the previously produced magnetic band with the carrier band does not require any special effort, the magnetic band itself being cheap to produce or to obtain. It is to be particularly stressed that, within the scope of the present invention, there is also included a magnetic layer applied directly to the carrier band.

In a particular further development of the present invention, the layer of magnetizable material is arranged on the carrier material in such a manner that, transversely to its direction of transport, it is at a distance from the test field material provided on the upper side. Preferably, it is arranged on the lower side of the carrier. Thus, between the magnetic layer and the test field material, there is an appropriate distance so that an undesirable mutual influencing during the production is avoided. Thus, for example, if heating is necessary for the application of the magnetic band, this does not adversely influence the test field material.

In order to achieve a high output in the production, by means of two recording heads, there are simultaneously recorded at least two magnetic tracks of data transversely to the direction of production. Due to this measure, which, ex post facto, appears to be simple, there is achieved a substantial increase of output in the production of the test strips.

In order to obtain a simply constructed apparatus for carrying out the process, the application of the amount of data takes place while the whole band is stationary. Movement of the whole band takes place, synchronised with the application of the amount of data, in a fixed-cycle operation, the movement in the direction of production being rhythmically stopped and, during the pauses, an amount of data is applied. The recording head or heads, as well as possibly reading-off heads, must merely be movable, by means of an appropriate device, transversely to the transport direction so that, in this regard, a comparatively small expense is necessary. Within the scope of the present invention, the advance of the whole band always takes place when a slider or the like carrying the recording head or heads, after application of an amount of data, returns to its starting position.

In an important embodiment of the present invention, in the case of the application of a new amount of data, there is simultaneously read off the amount of data applied in a preceding process stop. In this way, no additional time is needed for the reading-off by means of an appropriate reading head. Recording and reading-off head or heads are moved together by means of an appropriate device so that, in this regard, only a small expense for apparatus is needed.

In a special embodiment of the present invention, the recording speed, with which an amount of data is applied during the production, is greater, by a predetermined factor, than the read-off speed with which a previously recorded amount of data is read off in an evaluation device for the test strips. The production of a large number of strips per unit time of an economic production of individual test strips is thus achieved, the costs for a highly accurate and rapid device thereby being countered by the correspondingly large number of measurement strips produced. On the other hand, the evaluation device can have a comparatively simple construction, no high requirements having to be demanded with regard to the scanning of the amount of data because of the low speed of reading off.

In order to provide a correctly functioning and dependable device for carrying out the process, a driving unit can be provided with a slider movable transversely to the production direction of the band of carrier material, on which slider is provided at least one recording head for the application of an amount of data. This driving unit is controlled in such a manner that, in the case of stopping the said band, the transverse movement of the recording head takes place, an amount of data thereby being applied simultaneously. Thereafter, the band is further transported in the direction of production and, at the same time, the slider with the recording head is returned to its starting position. A quasicontinuous production is achieved but, on the basis of the stop-go manner of operation according to the present invention, an especially simple construction is achieved for the driving unit.

In a preferred further development of the present invention, on the movable slider there are arranged at least two recording and reading heads which, in the transport direction of the total band, are at a distance from one another, the distance thereby being synchronised with the hole distance of the band with the carrier material, an economic production thereby being ensured.

In an especially preferred embodiment of the present invention, the slider is movable by means of a sinusoidal drive which preferably has a sinusoidal guide path for the slider on a surface of a driving shaft. The driving shaft only turns in one direction of rotation, the slider thereby performing a back-and-forth movement transversely to the direction of transport. It will be appreciated that such a kind of driving unit ensures a high degree of functional safety and makes possible a rapid and dependable application of an amount of data in the case of a simple construction.

Since, in the case of a sinusoidal drive, the slider with the recording heads is not moved linearly, in the case of this preferred embodiment, a device is provided in order to synchronise the rhythm of the recording procedure corresponding to the slide movement. This includes a linear measure, preferably optical, securely attached to the slider, for the production of a rhythmic frequency proportional to the particular slider movement speed. These rhythms are utilised for the recording of the digital information on the magnetic strips so that this takes place slowly in the region of slow slider movement and quickly in the region of fast slider movement. The result is thus that the application of the information on to the test strips is spatially linear in spite of the non-linear slider movement.

A linear measure connected with the slider can, alternatively, be used electronically to control the slider drive in such a manner that the slider movement runs linearly in the region used for the magnetic recording.

In order that, in the case of recording an amount of date, there is ensured a definite alignment and placing of the band with the carrier material, it is preferably also provided that, by means of a preferably pneumatic device, the said band is pressed on to a base plate or the like. The flat placing of the band thereby achieved ensures a good contact between the recording head and the magnetic layer.

In a particular embodiment of the present invention, the recording head is arranged on a movable slider by means of an elastic spring element which, on the one hand, gives an exact alignment transversely to the direction of production and, on the other hand, gives an appropriate pressing-on force in the direction of the band. Additional spring elements can possibly also be provided in order to produce the pressing-on force. In a special further development of the present invention, the elastic spring element is constructed as a leaf spring which has recesses transversely to the direction of production and at a distance from the recording and reading-off head. Such a leaf spring gives a definite alignment of the recording or reading-off head transverse to the direction of transport. Furthermore, because of the recesses, a sufficient tiltability about the longitudinal axis of the leaf spring is permitted so that, in this regard, an adaptation to unevenesses or the like is possible. A high degree of dependability in the case of the application of an amount of data is thus achieved.

In accordance with the invention, a method of making a test strip with a longitudinally extending carrier and a test field comprises disposing a band of test field material on a broader band of carrier material substantially parallel to two longitudinal edges thereof. The method includes providing the band of carrier material in the region of at least one of the two longitudinal edges with a row of substantially equidistant recesses. The method also includes applying, in the production direction, onto the band of the carrier material, a layer of magnetizable material, and recording an amount of data for the storage of information in the layer of magnetizable material transversely to the production direction. The method also includes dividing up the band of carrier material transversely to the production direction into a plurality of longitudinally extending test strips.

Also in accordance with the invention, apparatus for making a test strip with a longitudinally extending carrier and a test field, a band of test field material being disposed on a broader band of carrier material substantially parallel to the longitudinal edges thereof, the band of the carrier material being provided with an amount of data for the storage of information, and the band being divided up transversely to the production direction into a plurality of longitudinally extending strips, the band of carrier material being provided in the region of at least one of its two longitudinal edges with a row of substantially equidistant recesses, and, onto the band of the carrier material therebeing applied, in the production direction, a layer of magnetizable material, comprises means for recording the amount of data in the layer of magnetizable material transversely to the production direction. The apparatus also includes means for dividing up the band of the carrier material transversely to the production direction into a plurality of longitudinally extending strips. The recording means comprises a drive unit including a slider movable transversely to the production direction, and at least one recording head on the slider for the application of an amount of data.

Also in accordance with the invention, a test strip comprises a test strip with a longitudinally extending carrier and a test field made by the method in accordance with the invention.

Further important features and advantages of the present invention are given in the following description of certain embodiments, reference being made to the accompanying drawings, in which.

Figure 1:
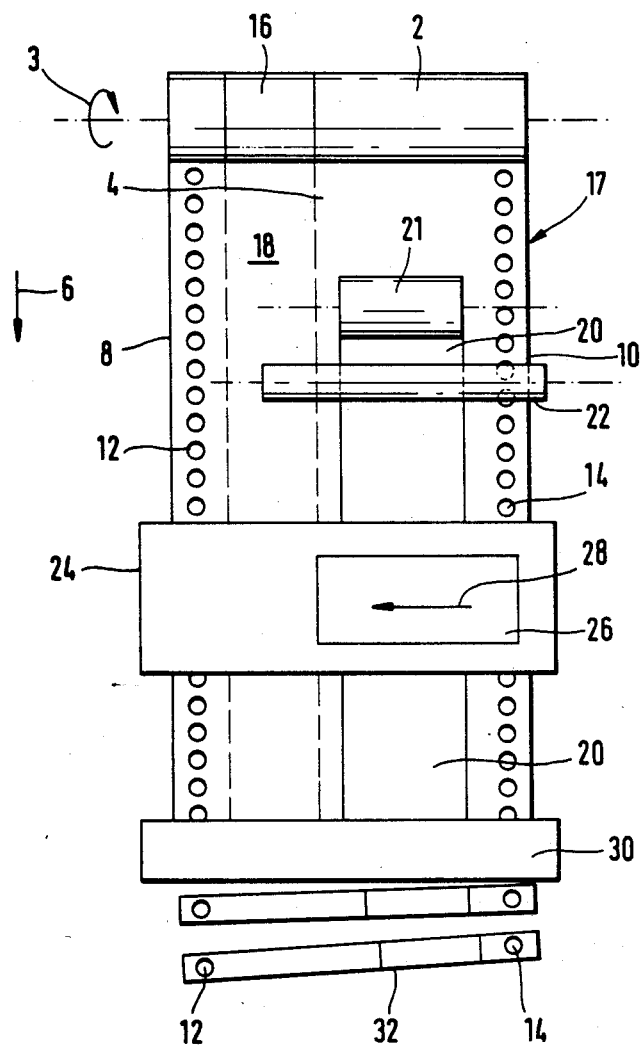
FIG. 1 is a schematic illustration of a device for carrying out the process according to the present invention.

FIG. 1 shows schematically a view of a device for carrying out the process according to the present invention. On a roll 2 is provided a band 4 of carrier material which can be wound off in the production direction indicated by arrow 6. The band 4 has, in the region of its longitudinal edges 8, 10, in each case a row of equidistant holes 12, 14. For the formation of the whole band 17, with the band 4 there is connected a band 16 of a test field material, the latter being narrower than the band 4 of the carrier material. On the here visible lower side 18 of the band 4, there is applied, in the form of a magnetic band, a layer 20 of magnetizable material. This can take place by means of a roller arrangement 21, 22, here only shown schematically, and/or by melt adhesion or by some other process. It is to be especially stressed that the application of the magnetizable layer, the introduction of the said rows of holes and also the connection of the test field material with the band of carrier material can be carried out in the sequence which, in any particular case, is the most preferred and can possibly also be carried out in separate working steps and/or at different places.

The band 4 of the carrier material, together with the layer 20 and band 16 of the test field material, is introduced into a driving unit 24. This driving unit 24 has appropriate transport means which, in cooperation with the holes 12, 14, make possible the transport of the band in the production direction 6. Furthermore, the driving unit 24 has, transversely to the production direction 6, a slider 26 movable back and forth which, in turn, has at least one recording head for the application of a particular amount of data to the layer 20 of magnetisable material. In the case of movement of the slider in the direction of the arrow 28, an amount of data is applied, the band 4 thereby being stationary. Subsequently, the band 4 is further transported and simultaneously the slider 26 is moved backwards in the opposite direction into its starting position.

In the production direction, behind the driving unit there is provided a cutting device 30 by means of which the individual test strips 32 are cut off. These longitudinal test strips 32 produced according to the present invention each have a hole 12, 14 in their ends. These holes 12, 14 define a reference direction which is decisive not only in the case of the recording of an amount of data but also in the case of the evaluation of an amount of data in an evaluation apparatus. By means of the said rows of holes, there is achieved an exact alignment of the band 4 with regard to the driving unit, this thereby ensuring a high degree of angular exactness in the case of the recording. Even when, in the case of cutting by means of the cutting device, inexactitudes arise due to the production process, these have no influence on the exactitude in the case of reading off an amount of data in an evaluation apparatus since the reference direction is pre-defined by means of the holes 12, 14 in the test strip.

Figure 2:
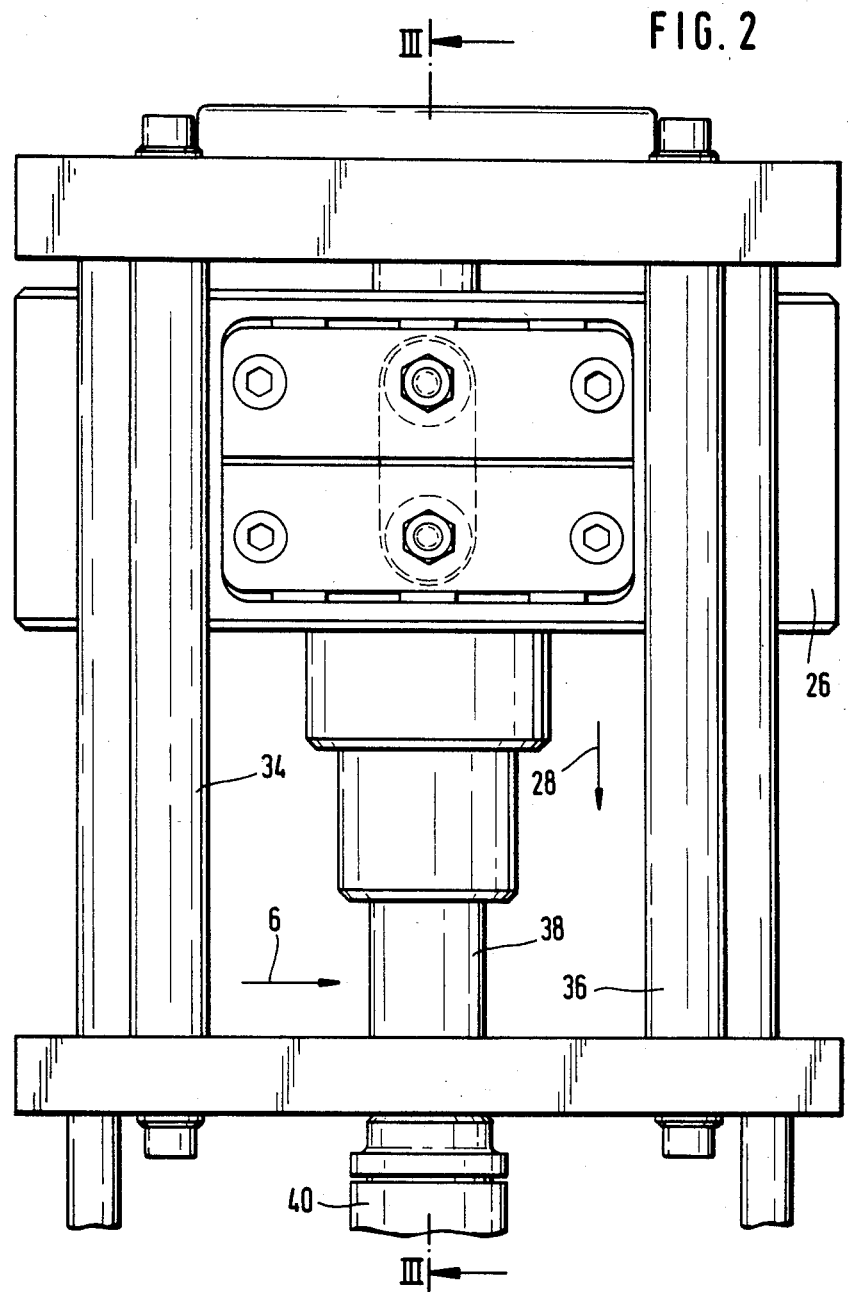
FIG. 2 is a view of a special driving unit which has a slider with recording and reading-off heads movable transversely to the direction of transport.

FIG. 2 shows, in part, a special embodiment of the driving unit 24 which, for the guiding of the slider 26 in the case of movement transverse to the transport direction 6, has two guide rods 34, 36. A drive shaft 38 is connected via a coupling 40 with an electric motor, which is here not illustrated. Rotation of the drive shaft brings about a back-and-forth movement of the slider in the direction of the arrow 28. Preferably, there is provided a sinusoidal drive, which is described hereinafter, but, in the scope of the present invention, other driving systems can also be used.

Figure 3:
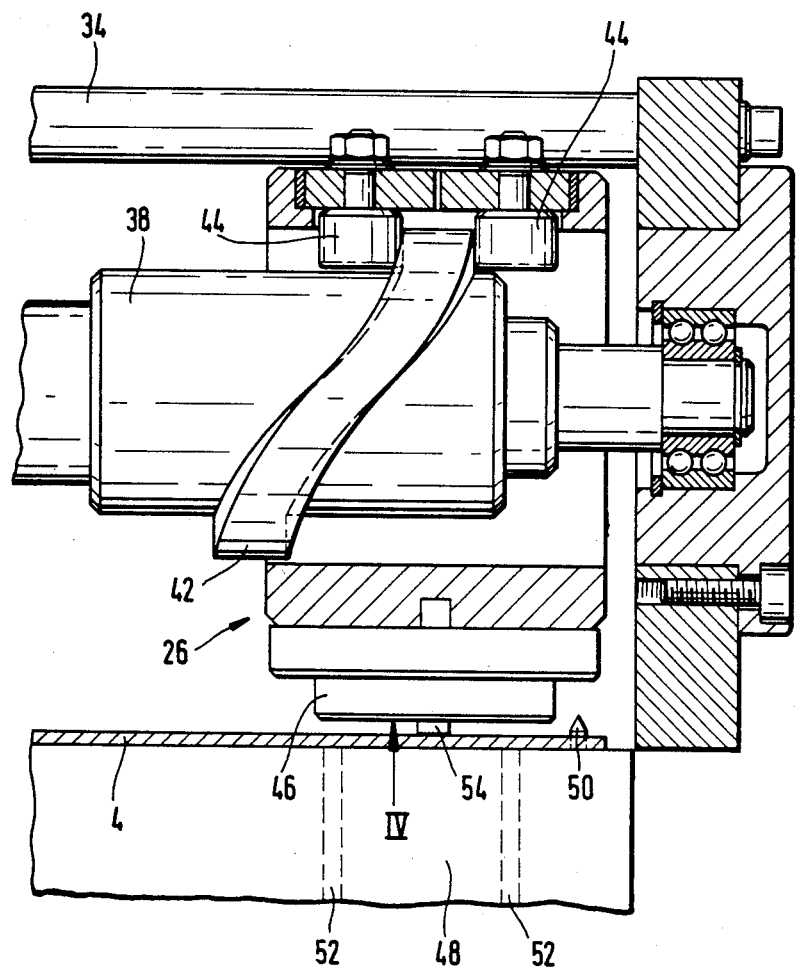
FIG. 3 is a partly sectional view of the driving unit according to FIG. 2 in the production direction, along the line III—III in FIG. 2.

FIG. 3 shows a view of a drive unit, partly in section, along the line III—III of FIG. 2. On the outer surface of the drive shaft 38, is here to be seen, in part, a sinusoidal guide path 42, the guide path 42 joining up behind the plane of the drawing. The slider 26 has rollers 44 in engagement with the guide path 42. In the case of rotation of the drive shaft 38 in one direction of rotation, the slider 26 performs the necessary back-and-forth movement. According to the present invention, the recording of an amount of data takes place in the case of a substantially uniform movement of the slider. With the provided drive unit, the heavy slider can simultaneously be moved very quickly and guided precisely in order to achieve a high speed of working. The application of an amount of data is synchronised corresponding to the movement of the slider 26, the movement of the recording head being picked up with a linear measure. In the drawing, there is to be seen a plate 46 which is present vertically over a horizontally directed base plate 48. By means of a conical pin 50, which engages in the above-described holes 12, 14 of the band 4, there takes place a definite alignment of the band 4. In the base plate 48, there are present holes 52 which enable a pneumatic sucking of the band 4 on to the base plate. On the lower side of the plate 46, there is here to be seen a recording head 54.

Figure 4:
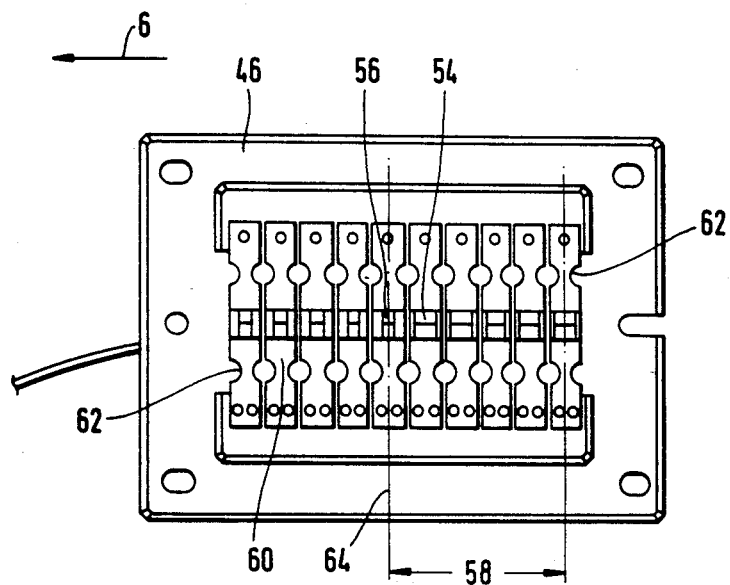
FIG. 4 is a view in the direction IV indicated in FIG. 3 of a plate of the slider with several recording and reading-off heads.

FIG. 4 shows a view of the plate 46 of the slider, whereby here, in the production direction (arrow 6), there are arranged side-by-side in each case 5 recording heads 54, as well as five reading-off heads 56. By means of recording heads 54, five amounts of data are thus simultaneously recorded in five parallel tracks. After the transport of the band 4 (here not illustrated) corresponding to the distance 58 between the first recording head 54 and the first reading-off head 56, the magnet tracks in the magnetic layer are present directly under the reading-off head 56. In the case of subsequent movement of the slider and the recordal of further magnetic tracks, by means of the reading heads 56, the previously recorded amount of data on the magnet tracks are read off. If faults are hereby ascertained, then an appropriate marking is carried out so that, after cutting up the band, the corresponding faulty test strips can be sorted out. The recording and reading heads 54, 56 are arranged on longitudinal leaf springs 60 which, laterally of the recording and reading heads 54, 56, have recesses or inlets 62. A cardan-like suspension of the recording or reading heads 54, 56 is achieved, a definite alignment in the direction of the longitudinal axis 64 of the leaf springs 60 thereby being ensured. On the other hand, a sufficient movability of the heads about this longitudinal axis 64 and also vertically to the plane of the drawing is provided. It is to be stressed that the longitudinal axis 64, in the scope of the present invention, is aligned with the axis defined by opposite-lying holes in the band of carrier material. The recording direction of an amount of data agrees to the greatest possible extent with the reference direction defined by opposite-lying holes in the band of carrier material so that angular errors in the case of the recording can be dependably-avoided.

Figure 5:
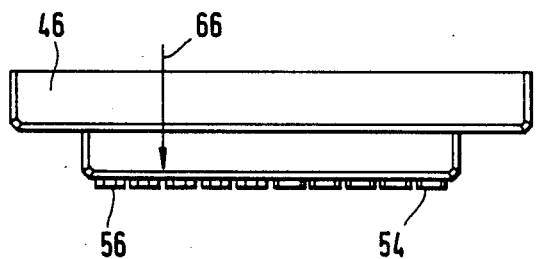
FIG. 5 is a side view of the plate according to FIG. 4.

FIG. 5 shows a side view of the plate 46 with a total of ten recording and reading-off heads 54, 56. In order to ensure a dependable lying of the recording and reading-off heads 54, 56 on the magnetic layer, in addition to the above-mentioned leaf springs, there can, in each case, be provided further spring elements which, in the direction of the arrow 66, press the individual heads onto the magnetic layer in order to obtain an intimate contact.

While there has been described what is at present considered to be the preferred embodiment of this invention, it will be obvious to those skilled in the art that various changes and modifications may be made therein without departing from the invention, and it is, therefore, aimed to cover all such changes and modifications as fall within the true spirit and scope of the invention.

What is claimed is:

1. A method of making a test strip with a longitudinally extending carrier and a test field, comprising:
   disposing a band of test field material on a broader band of carrier material substantially parallel to two longitudinal edges thereof;
   providing said band of said carrier material with a first row of substantially equidistant recesses in the region of one of said two longitudinal edges and with a second row of substantially equidistant recesses in the region of the other of said two longitudinal edges;
   applying onto said band of said carrier material a layer of magnetizable material;
   recording by means of a recording head an amount of data for the storage of information in said layer of magnetizable material transversely to the production direction, said carrier band being positioned and aligned by means of said first and second recesses during that recording step; and dividing up said band of said carrier material transversely to said production direction into a plurality of longitudinally extending test strips in such a manner that said recesses are close to the ends of each strip.

2. A method according to claim 1, in which the step of recording an amount of data comprises recording simultaneously transversely to said production direction, at least two magnet tracks of said amount of data.

3. A method according to claim 1, wherein the step of applying said layer of magnetizable material comprises applying said layer of said magnetizable material in the form of a previously produced magnetic band by adhesion, melt adhesion or the like.

4. A method according to claim 1, wherein the step of applying said layer of said magnetizable material comprises applying said layer of magnetizable material to said band of said carrier material at a distance from said band of said test field material.

5. A method according to claim 4, wherein the step of applying said layer of said magnetizable material comprises applying said layer of magnetizable material to said band of said carrier material on the side opposite to the disposition of said band of said test field material.

6. A method according to claim 1, comprising:
before dividing up said carrier band into test strips, reading off for testing purposes the recorded amount of data by means of a reading off head distanced apart from said recording head in said production direction, the distance between said recording head and the corresponding reading off head being an integral multiple of the distance between said substantially equidistant recesses in said band of carrier material; and
when an error is ascertained, carrying out a marking or the like so that a faulty test strip can be sorted out after the dividing up by means of the marking.

7. A method according to claim 6, wherein recording an amount of data and reading-off of a previously recorded amount of data takes place while the whole band is stationary.

8. A method according to claim 6, wherein the speed of recording of an amount of data during the production is greater by a predetermined factor than the reading-off speed in the case of evaluation of a previously recorded amount of data in an evaluation device.

9. A method according to claim 1, in which the step of recording comprises recording by means of a recording head having an instantaneous speed, the recording being synchronized with a frequency which is proportional to said instantaneous speed of said recording head.

10. Apparatus for making a test strip with a longitudinally extending carrier and a test field, a band of test field material being disposed on a broader band of carrier material substantially parallel to the longitudinal edges thereof, the band being divided up, transversely to the production direction, into a plurality of longitudinally extending test strips, the band of carrier material being provided in the region of at least both of its two longitudinal edges with a row of substantially equidistant recesses and, onto the band of the carrier material there being applied, in the production direction, a layer of magnetizable material, the apparatus comprising:

means for recording an amount of data for the storage of information in the layer of magnetizable material transversely to the production direction; and
means for dividing up the band of the carrier material transversely to the production direction into a plurality of longitudinally extending test strips;
said recording means comprising a drive unit including a slider movable transversely to the production direction, and at least one recording head on said slider for the application of an amount of data.

11. Apparatus according to claim 10, including on said slider at least two recording and reading-off heads distanced apart in the production direction, the distance between a recording head and the corresponding reading-off head being an integral multiple of the distance between the substantially equidistant recesses in the band of carrier material.

12. Apparatus according to claim 10, comprising:
means for pressing the band of carrier material, in the region of at least one recording head, against a flat base plate during the recording of an amount of data.

13. Apparatus according to claim 12, wherein said pressing means comprises means for pressing the band of carrier material pneumatically against the flat base plate.

14. Apparatus according to claim 10, comprising:
an elastic spring element which disposes said at least one recording head on said slider and which gives an exact alignment transversely to the production direction and also provides a predetermined pressing force onto the layer of the band of carrier material.

15. Apparatus according to claim 14, wherein said elastic spring element comprises a leaf spring which, transversely to the production direction and distanced from the recording head, has recesses.

16. A test strip with a longitudinally extending carrier and a test field, made by the method comprising:
disposing a band of test field material on a broader band of carrier material substantially parallel to two longitudinal edges thereof;
providing said band of said carrier material with a first row of substantially equidistant recesses in the region of one of said two longitudinal edges and with a second row of substantially equidistant recesses in the region of the other of said two longitudinal edges;
applying onto said band of said carrier material a layer of magnetizable material;
recording by means of a recording head an amount of data for the storage of information in said layer of magnetizable material transversely to the production direction, said carrier band being positioned and aligned by means of said first and second recesses during that recording step; and
dividing up said band of said carrier material transversely to said production direction into a plurality of longitudinally extending test strips in such a manner that said recesses are close to the ends of each strip.

17. A test strip according to claim 16, wherein the step of applying said layer of magnetizable material comprises applying said layer of said magnetizable material in the form of a previously produced magnetic band by adhesion, melt adhesion or the like.

18. A test strip according to claim 16, wherein the step of applying said layer of said magnetizable material comprises applying said layer of magnetizable material to said band of said carrier material at a distance from said band of said test field material.

19. A test strip according to claim 18, wherein the step of applying said layer of said magnetizable material comprises applying said layer of magnetizable material to said band of said carrier material on the side opposite to the disposition of said band of said test field material.

20. A test strip according to claim 16, in which the step of recording an amount of data comprises recording simultaneously transversely to said production direction, at least two magnet tracks of said amount of data.

21. A test strip according to claim 16, the method comprising:
before dividing up the band into test strips, reading off for testing purposes the recorded amount of data; and,
when an error is ascertained, carrying out a marking or the like so that a faulty test strip can be sorted out after the dividing up by means of the marking.

22. A test strip according to claim 21, wherein recording an amount of data and reading-off of a previously recorded amount of data takes place while the whole band is stationary.

23. A test strip according to claim 21, wherein the speed of recording of an amount of data during the production is greater by a predetermined factor than the reading-off speed in the case of evaluation of a previously recorded amount of data in an evaluation device.

24. A test strip comprising:
a longitudinally extending carrier and a test field; and
a layer of magnetizable material on said carrier in which an amount of data for the storage of information has been applied in the longitudinal direction of said magnetizable material, said carrier having a recess near each end thereof.

25. A test strip for analytical evaluations comprising:
an elongated synthetic resin carrier strip having first and second opposed surfaces and first and second opposed ends,
a piece of test field material on said first surface, close to said first end,
a layer of magnetisable material on said second surface, spaced a distance from the piece of test field material,
said layer of magnetisable material storing at least 500 bit of data for said analytical evaluations,
said data having been recorded in said layer in a longitudinal direction of said strip, and
a first recess at said first end and a second recess at said second end, said first and second recesses being adapted to provide a required alignment and positioning of said strip in the analytical evaluations.

26. A test strip for analytical evaluation comprising:
a carrier having first and second opposed support surfaces and first and second opposed ends;
a test field zone on said first surface close to said first end;
a zone of magnetizable material on said carrier;
said zone of magnetizable material storing data for said analytical evaluation; and
a recess at least at said first end and at said second end of said carrier, said recesses at said first and second ends being in opposed relationship and being adapted to provide a required alignment and positioning of said strip.

27. A test strip according to claim 26, wherein said zone of magnetisable material is on said second surface.

28. A test strip according to claim 26, wherein said zone of magnetisable material stores at least 300 bit of said data.

29. A test strip according to claim 26, wherein said zone of magnetisable material is spaced apart from said test field zone.

30. A process for the production of test strips which comprises:
(a) providing a band of a carrier material having first and second opposed support surfaces and first and second opposed longitudinal edges and a band of test field material narrower than said band of carrier material disposed on said first surface parallel to said longitudinal edges;
(b) a step of forming a row of equidistant recesses in said band of carrier material at least in the regions of said first and second longitudinal edges;
(c) a step of applying a layer of magnetizable material to said band of carrier material; and storing data in said layer; and
(d) as a final step, dividing the formed band transversely of its length into a plurality of strips, there being at least one of said recesses at a first end of each strip and a second recess at a second end of each strip.

31. A process according to claim 30, wherein step (c) comprises applying said layer of magnetizable material in a longitudinal direction of said band of carrier material and recording said data in said layer, transversely of said band of carrier material.

32. A process according to claim 31, wherein step (c) comprises applying said layer to said second surface, and wherein step (b) is carried out prior to step (c) and said band of carrier material is positioned and aligned for steps (c) and (d) by means of said first and second rows of equidistant recesses.

* * * * *

UNITED STATES PATENT AND TRADEMARK OFFICE
CERTIFICATE OF CORRECTION

PATENT NO. : 4,578,716
DATED : March 25, 1986
INVENTOR(S) : Rainer van Rijckevorsel et al.

It is certified that error appears in the above-identified patent and that said Letters Patent is hereby corrected as shown below:

Column 1, line 65 for "of" read -- or --.

Column 5, line 23 for "date" read -- data --.

Signed and Sealed this

Ninth Day of September 1986

[SEAL]

Attest:

DONALD J. QUIGG

Attesting Officer      Commissioner of Patents and Trademarks